United States Patent
Cyprien et al.

(10) Patent No.: US 7,186,269 B2
(45) Date of Patent: Mar. 6, 2007

(54) COMPOSITE SHOULDER PROSTHESIS

(76) Inventors: Jean-Maxwell Cyprien, 11, rue du Conseil-General, Geneva (CH) 1205; André Burdet, Les Condemines, Corcelles prés Payerne (CH) 1562; Jean-Dominique Demottaz, 7, chemin des Serres, Vessy (CH) 1234; Jean-Claude Bonvin, 1, rue Lamartine, Geneva (CH) 1203; Bernard Neuhaus, 12, Rüschlistrasse, Biel (CH) 2502

( * ) Notice: Subject to any disclaimer, the term of this patent is extended or adjusted under 35 U.S.C. 154(b) by 0 days.

(21) Appl. No.: 10/439,228

(22) Filed: May 16, 2003

(65) Prior Publication Data

US 2004/0230311 A1 Nov. 18, 2004

(51) Int. Cl.
*A61F 2/40* (2006.01)
(52) U.S. Cl. .................. 623/19.11; 623/19.14
(58) Field of Classification Search .......... 623/19.11, 623/19.12, 19.13, 19.14, 22.42, 22.43, 22.44, 623/22.45, 223.12, 23.14, 23.28
See application file for complete search history.

(56) References Cited

U.S. PATENT DOCUMENTS

| | | | |
|---|---|---|---|
| 3,228,393 A | | 1/1966 | Michele |
| 4,919,670 A | * | 4/1990 | Dale et al. ............. 623/19.14 |
| 4,938,771 A | * | 7/1990 | Vecsei et al. ............ 623/23.15 |
| 5,728,161 A | * | 3/1998 | Camino et al. .......... 623/22.41 |
| 5,944,758 A | | 8/1999 | Mansat et al. |
| 6,165,224 A | * | 12/2000 | Tornier .................. 623/23.21 |
| 6,171,341 B1 | * | 1/2001 | Boileau et al. .......... 623/19.11 |
| 6,334,874 B1 | | 1/2002 | Tornier et al. |
| 6,368,352 B1 | | 4/2002 | Camino et al. |
| 6,398,812 B1 | | 6/2002 | Masini |
| 6,406,496 B1 | | 6/2002 | Ruter |
| 6,899,736 B1 | * | 5/2005 | Rauscher et al. ........ 623/19.12 |

FOREIGN PATENT DOCUMENTS

DE 4220217 12/1993

OTHER PUBLICATIONS

Authors: GAzdag A.R., Lane J.M., Glaser D., et al.
Title: Alternatives to sutogerious bone graft.
Journal of the American Academy of Orthopedic Surgeons 3: p. 2, Table1, 1995.

* cited by examiner

Primary Examiner—David H. Willse
Assistant Examiner—Javier G. Blanco

(57) ABSTRACT

The invention is a modular composite shoulder prosthesis 64, whose construct incorporates a solid autogenous bone graft 50 to be used to replace the upper humerus in certain fracture types. The prosthesis comprises a stem 22 to be inserted in the canal of the humerus, an intermediary part reduced to a medial pillar 24 and a head which is a generally spherical cap 20 that is hollow. The head of the prosthesis being hollow and coated with an osteoconductive material, the lateral aspect of the medial pillar as well as the upper part of the stem being also coated with the same material, an epiphyso-metaphyseal space is delineated in which a solid autogenous bone graft is fitted. Union can be achieved between the coated parts of the prosthesis, the bone graft 50 and the tuberosities reattached to the humerus shaft, secured to holes 62 of the medial pillar and between themselves.

13 Claims, 12 Drawing Sheets

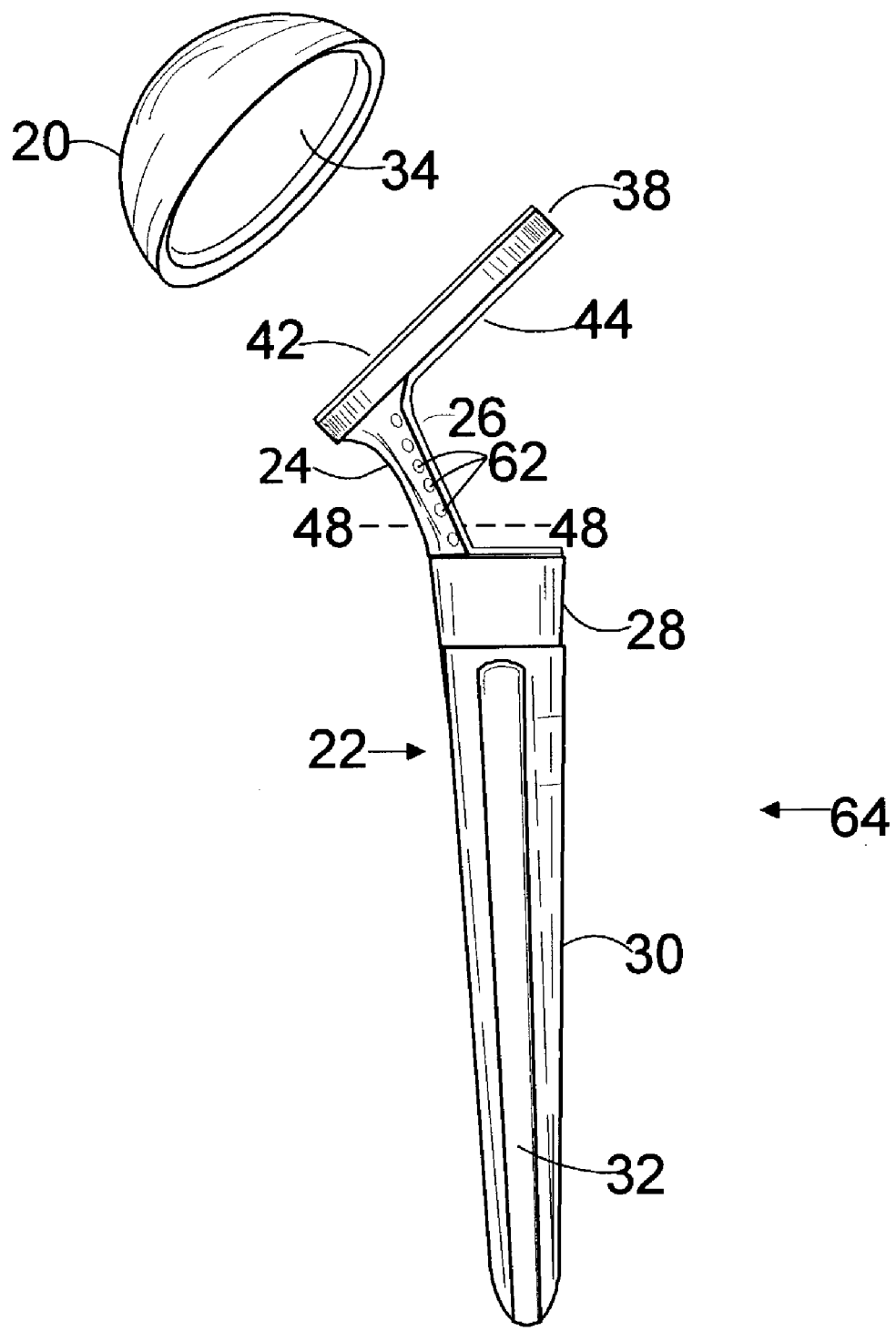
Fig. 4-A

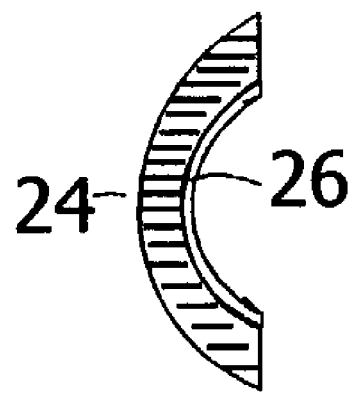
Fig. 4-B

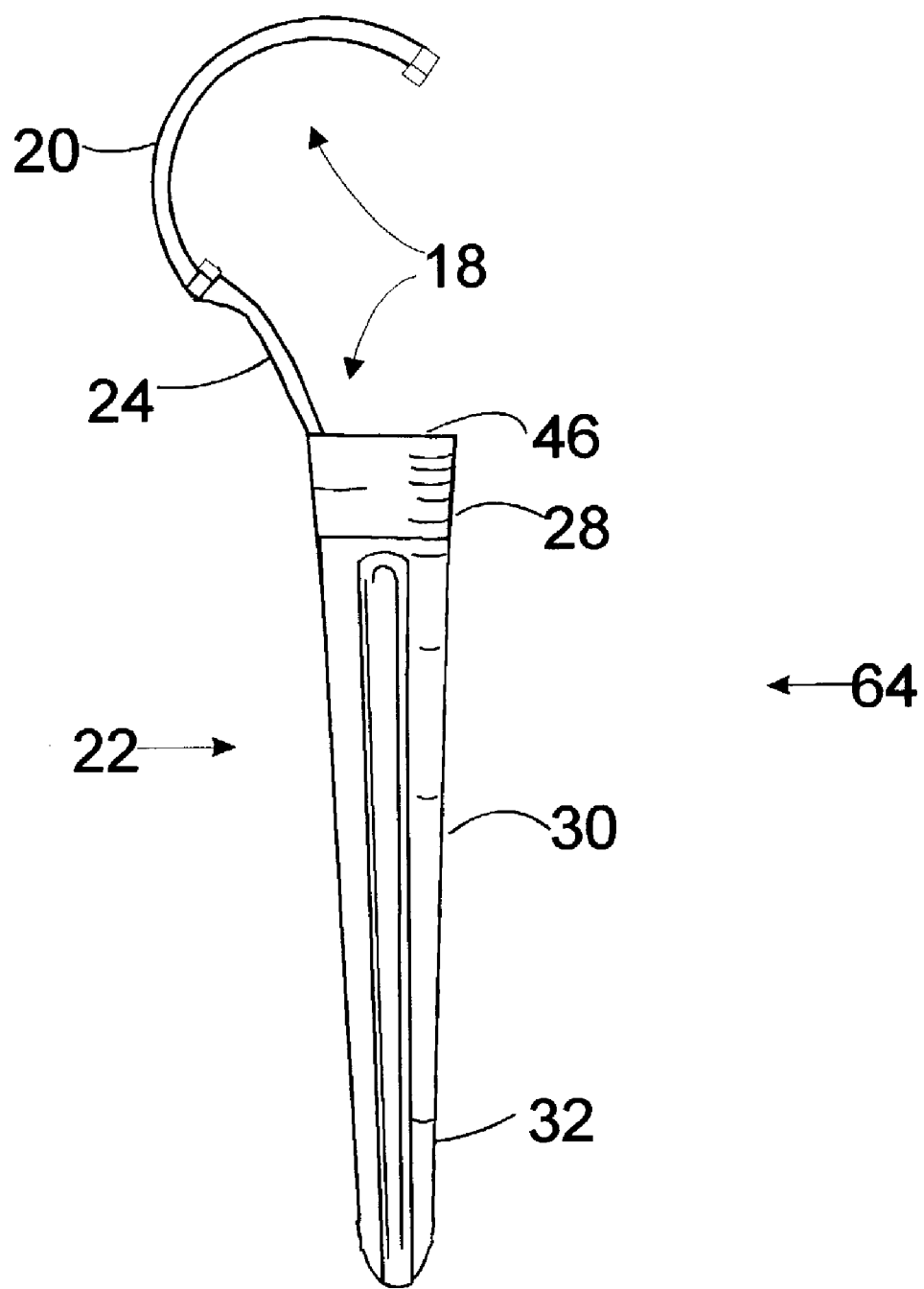
Fig. 8-A

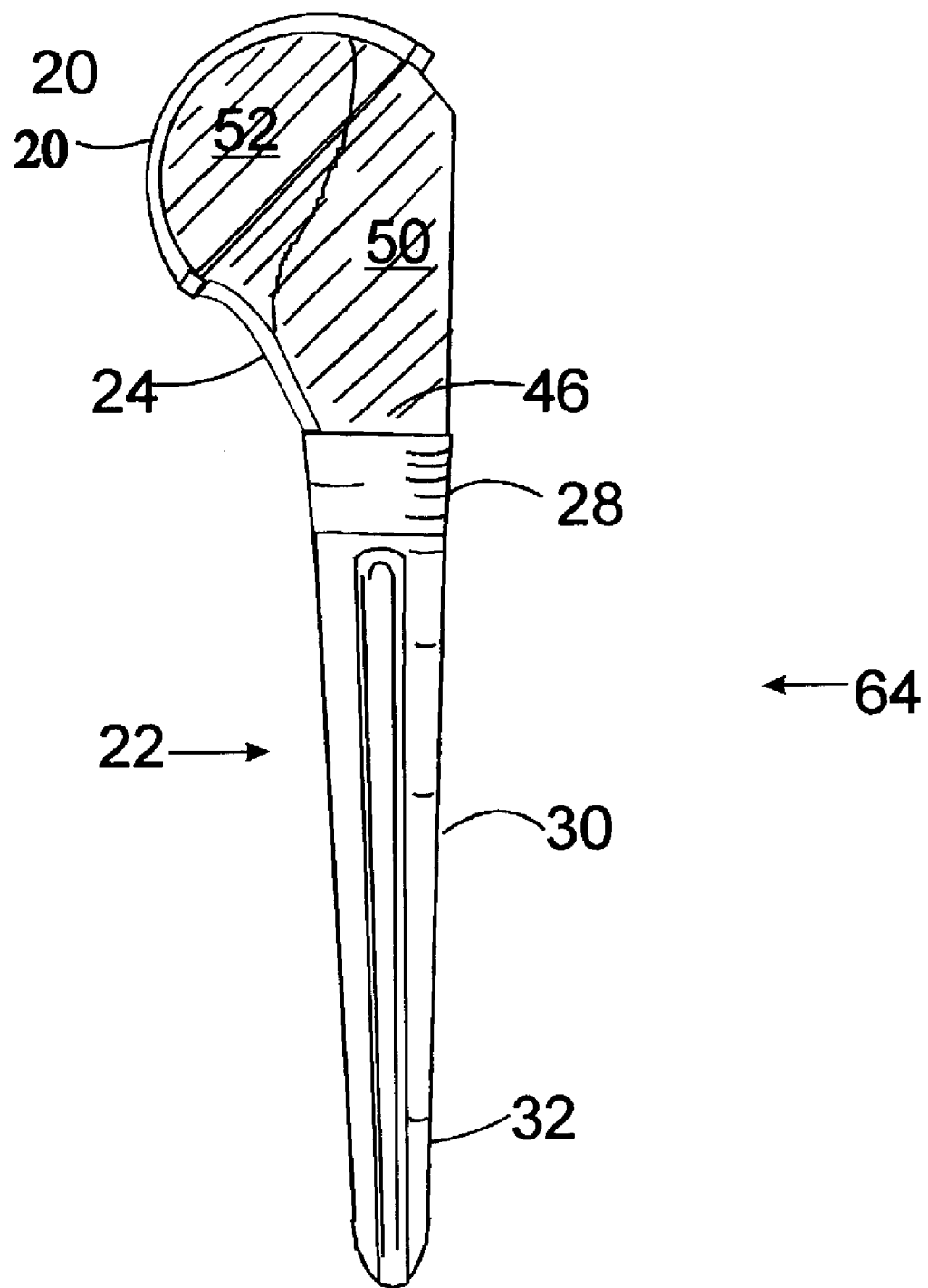
Fig. 8-B

COMPOSITE SHOULDER PROSTHESIS

CROSS-REFERENCES TO RELATED APPLICATIONS

| U.S. Pat. DOCUMENTS | | |
|---|---|---|
| 6,334,874 | Tornier, et al. | Jan. 1, 2002 |
| 6,406,496 | Ruter | Jun. 18, 2002 |
| 6,398,812 | Masini | Jun. 4, 2002 |
| 6,368,352 | Camino, et al | Apr. 9, 2002 |
| 6,171,341 | Boileau et al. | Jan. 9, 2001 |
| 5,944,758 | Mansat, et al | August 1999 |
| 3,228,393 | Michele | Jan. 11, 1966 |
| FOREIGN PATENT DOCUMENT: | | |
| DE 4220217 | Ruether, et al | Dec. 23, 1993 |

FEDERALLY SPONSORED RESEARCH

Not applicable

SEQUENCE LISTING OR PROGRAM

Not applicable

BACKGROUND OF THE INVENTION

Replacement of diseased or injured joints is common practice in orthopedic surgery. The replacement of a shoulder joint either for arthritic disease or for fracture by an artificial device can restore function in many cases.

Shoulder prostheses can be implanted in the presence of the so-called "four part humeral fractures". In those fractures of the proximal part of the humerus, the humeral head, the greater tuberosity and the lesser tuberosity separate from the humeral shaft. This results in the four parts fractures described by Neer. In such cases, it is common practice to use shoulder prosthesis to reconstruct the proximal part of the humerus. However, if replacing the humeral head is relatively easy, reattaching the tuberosities often results in failure of those parts to unite to the rest of the humerus or in their union in an inappropriate position. Bad functional outcome of shoulder replacement for fracture seems to be directly correlated to this phenomenon. A number of prosthesis have been described and used to solve the problem. Among others, see for instance U.S. Pat. No. 6,171,341 and No. 5,944,758, No. 6,283,999. In those devices there are various means to keep the tuberosities in position until union. The U.S. Pat. No. 6,334,874 B1, like U.S. Pat. No. 3,228,393 for a femur prosthesis, has a metaphyseal portion with window in which a bone graft can be inserted and U.S. Pat. No. 6,171,341 has a metaphyseal portion comprising only a medial branch thereby having an area in which a bone graft can be used. In those two devices a better contact between the fractured fragments is sought. However, in the prior art, the stability of the fragments necessary to fracture healing and the provision of abundant biological material necessary to induce the union of the bony fragments are not simultaneously provided.

In another aspect of shoulder prosthesis designing relevant to the present invention, U.S. Pat. No. 6,368,352, in order to diminish the weight of the implant, has a closed space defined between the collar and the modular head in an assembled configuration while DE patent No 4220217 has a head which is a cap with a central shaft and an inner surface with open cell or a porous structure.

In the present invention, the space of the hollow head is completely open in order to accommodate bone grafts.

The object of the invention is to restore shoulder function after three or four parts humeral fractures by providing an improved prosthesis to bring about the union of the separated tuberosities to the upper humerus while replacing the broken humeral head. To do so a modular composite shoulder prosthesis is described whose construct incorporates a solid autogenous bone graft. The prosthesis comprises a stem to be inserted in the medullary canal of the humerus, an intermediary part with a number of holes and a head that is hollow. The head of the prosthesis being a hollow spherical cap with an inner lining of an osteoconductive material, that is, a material conductive to bone ingroth the lateral aspect of the medial pillar as well as the upper part of the stem being also coated with the same material, a large epiphyso-metaphyseal space is created in which a solid autogenous bone graft usually from the iliac crest can be impacted. Union can be achieved between the prosthesis and the autogenous iliac bone graft on one side and between the iliac bone graft, the tuberosities reattached to the humerus shaft, to the intermediary portion and between themselves by multiple sutures and/or wires. The bone graft is considered as a part of the prosthesis both from a mechanical and from a biological perspective.

This composite shoulder prosthesis results in the following:

1. a structure formed by the cap, the ring, the medial pillar and the stem, that provides a smooth spherical surface together with mechanical support and stability;
2. an osteoconductive coating that provides a framework amenable to the ingrowth of blood vessels and osteoprogenitor, type of bone cell consisting of undifferentiated cells from which the osteoblasts, the bone-forming cells, are derived;
3. osteoinductive factors brought by the iliac graft for the induction or the modulation of bone formation;
4. osteogenic cells, graft cells from the iliac bone graft that can differentiate into osteoblasts.

Accordingly, the mechanical and biological conditions to facilitate the union process between those humeral tuberosities, the composite prosthesis, and the remainder of the humerus are optimally set.

In certain cases in which the harvesting of the iliac bone graft is considered of an excessive morbidity, the prosthesis is also provided with a scaffold of an osteoconductive material, scaffold in which bone chips from the broken humeral head can be positioned for bone induction.

BRIEF SUMMARY OF THE INVENTION

This invention relates to a shoulder prosthesis for upper humeral fractures that comprises a stem part to be fixed in the medullary canal of the upper humerus. The stem is extended upwards by a medial pillar on which is attached at an angle a ring. This ring has on its upper, lower and inner aspects a lining of an osteoconductive material. On the ring is fixed a modular hollow head whose cavity also has an inner lining made of an osteoconductive material.

This construct delineate an open epiphyso-metaphyseal space in which an iliac bone graft is impacted while bone chips from the broken humeral head are used to complete the filling of the head of the prosthesis. The result achieved is a composite shoulder prosthesis whose lateral part is made of autologous graft on which the tuberosities can be fixed in a bone to bone full contact fashion.

The invention also relates to a method of treating a fracture of an uppper humerus with a separation of a humeral head and of tuberosities comprising plurality of steps:
a. harvesting an autocienous iliac bone graft:
b. removing a broken humeral head:
c. providing a shoulder prosthesis
d. filling with said iliac bone graft and chips from said broken humeral head the space coated with an osteoconductive material of the shoulder prosthesis
e. inserting and cementing said shoulder prosthesis
f. attaching separated portions of tuberosities of the broken upper part of the humerus to the remainder of the humerus, to said shoulder prosthesis and between themselves, whereby achieving a composite shoulder prosthesis construct with a smooth surfaced spherical cap on the medial side and an area of autogenous bone on the lateral, anterior and posterior sides to which the tuberosities can unite.

Considering the potential morbidity of iliac bone graft harvesting, the composite shoulder prosthesis may alternatively be provided with a metaphyseal scaffold of material conductive to bone ingrowth as a substitute for the autoloqous iliac bone graft. In said scaffold, bone chips from the broken humeral head can be positioned for osteoinduotion.

BRIEF DESCRIPTION OF THE SEVERAL VIEWS OF THE DRAWING

Notes:
1. Positional references such as anterior/posterior, medial/lateral, proximal/distal and upper/lower used herein are made with reference to the prosthesis as it would be positioned in a left shoulder.
2. Details of design, manufacture and procedure may be modified without departing from the spirit, intent and scope of the invention described herein.

Embodiments of the invention are described in more detail in the next section using the drawings. There are shown in:

FIG. 4-A: a front elevational view of the shoulder prosthesis showing the various parts of the prosthesis.

FIG. 4-B: a cross sectional view of the medial pillar.

FIG. 8-A: a sectional view of the empty proximal part of the prosthesis.

FIG. 8-B: a sectional view of the proximal part of the prosthesis after positioning the graft and the bone chips.

DETAILED DESCRIPTION OF THE INVENTION

Figure 1:
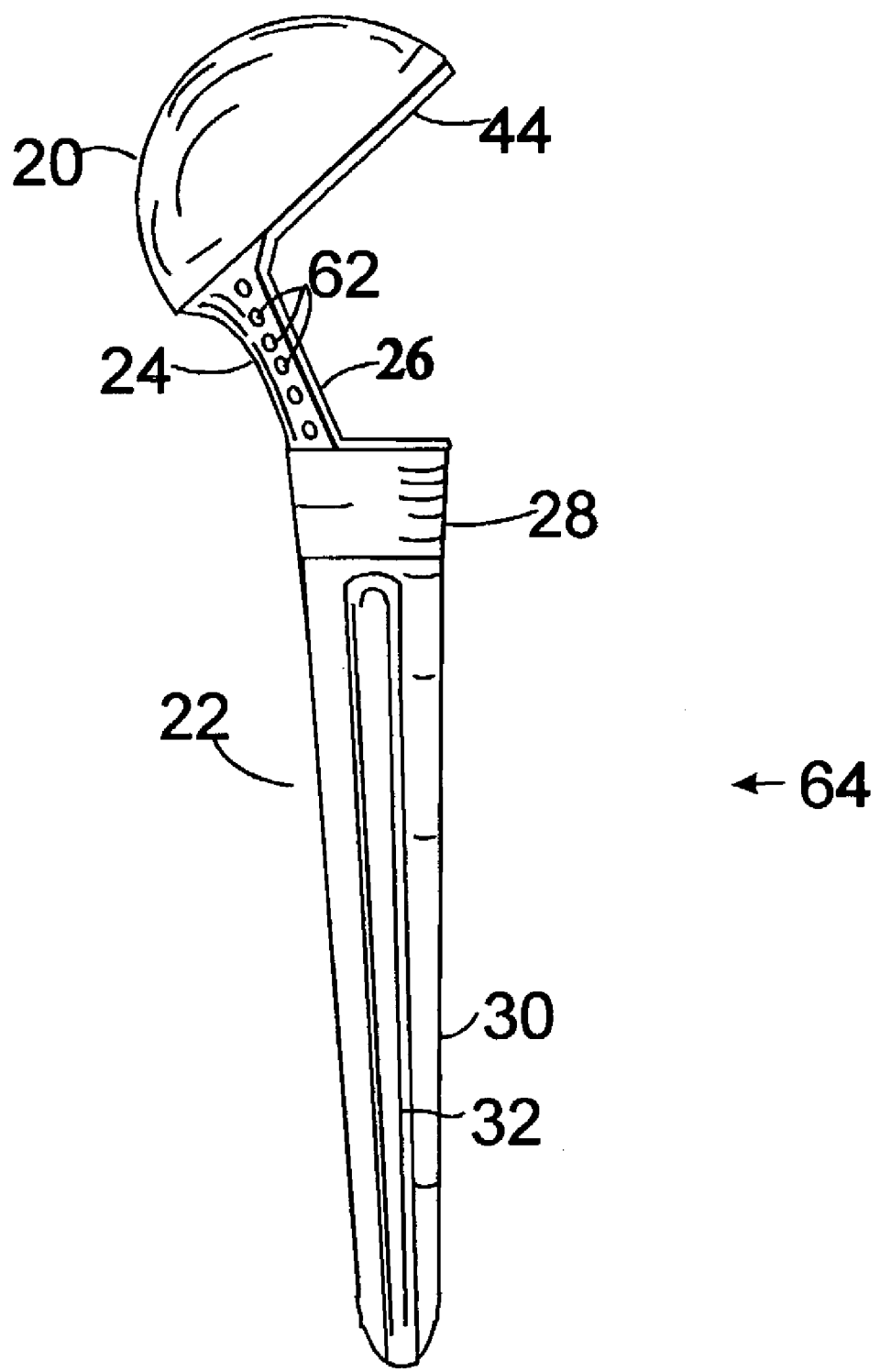
FIG. 1: a front elevational view of the shoulder prosthesis

FIG. 1 shows the shoulder prosthesis 64 according to the invention. It is made of a head, which is a generally spherical cap 20 and a stem 22 with a medial pillar 24 with on its lateral aspect a coating of a material 26 that allows for bone ingrowth and holes 62 to attach an iliac bone graft and the tuberosities.

The stem 22, on its most upper part 28, is coated with a material that allows for bone ingrowth and its lower part 30 is made of metal to allow cementation. It has longitudinal grooves 32 to facilitate cementation.

Figure 2:
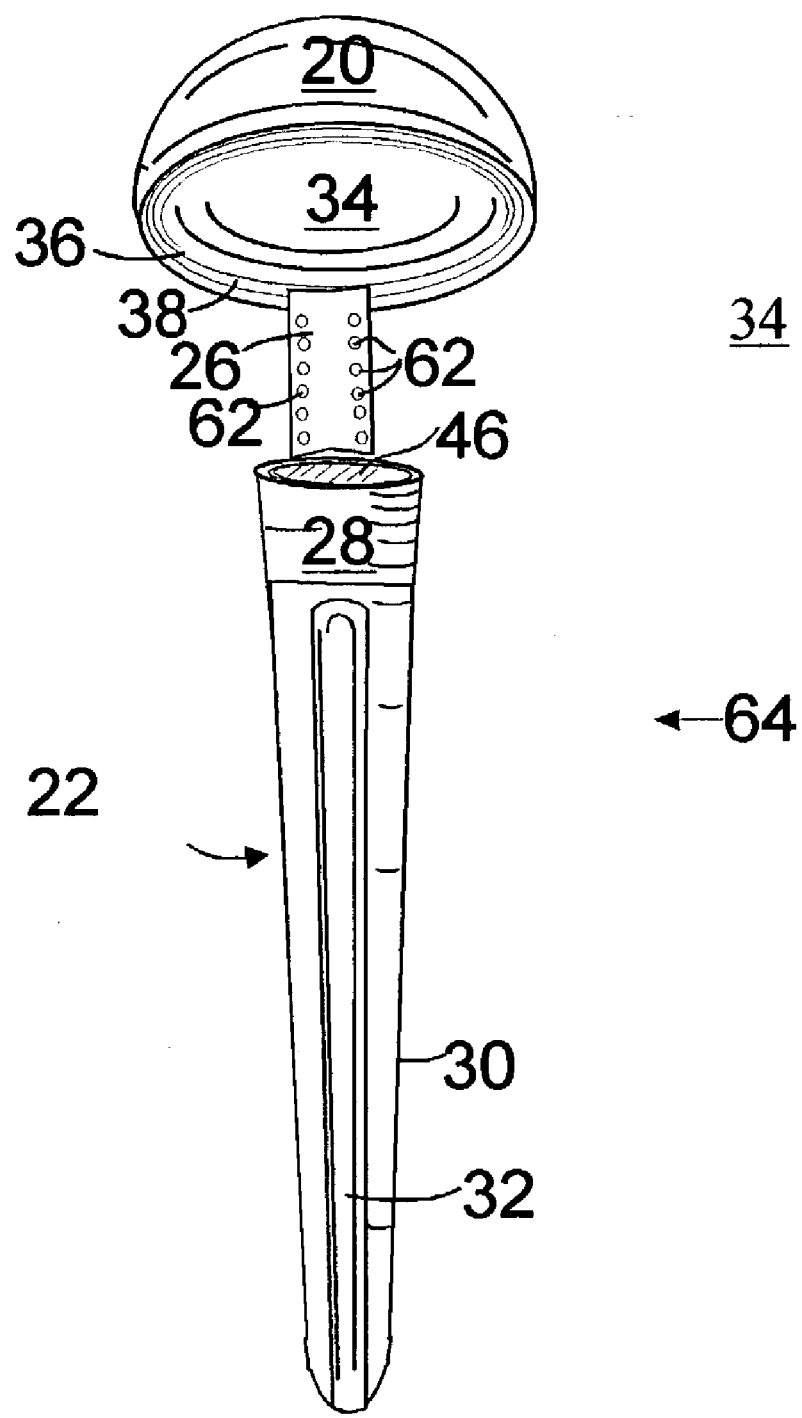
FIG. 2: a right elevational view of the prosthesis showing the inside of the head and of the ring as well as the coating of the medial pillar.

FIG. 2 is a right elevational view of the prosthesis 64 showing the inner lining 34 of the spherical cap 20, the inner lining 36 of the ring 38, of the medial pillar 26, the coating of the upper part 28 of the stem 22 and its slightly hollow coated superior aspect 46.

Figure 3:
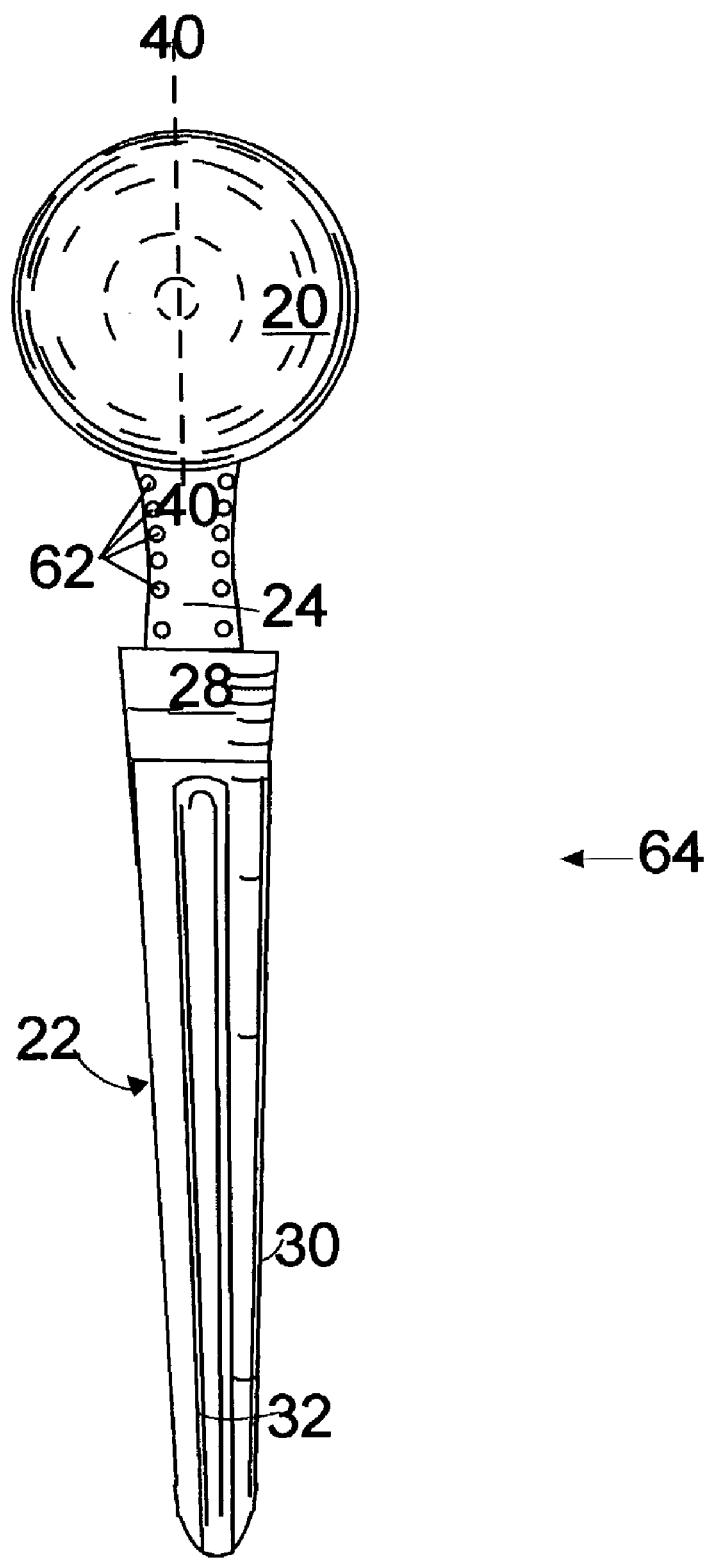
FIG. 3: a left elevational view of the prosthesis showing the medial aspect of the head and of the medial pillar.

FIG. 3 is a left elevational view of the prosthesis 64 showing the medial aspect of the spherical cap 20 and of the medial pillar 24.

FIG. 4-A shows parts of the prosthesis 64:
the spherical cap 20 which is the head of the prosthesis 64 and its inner lining 34,
the ring 38 on which the head 20 is to be attached,
the lining on the upper 42 and lower 44 surface of the ring.

Figure 5:
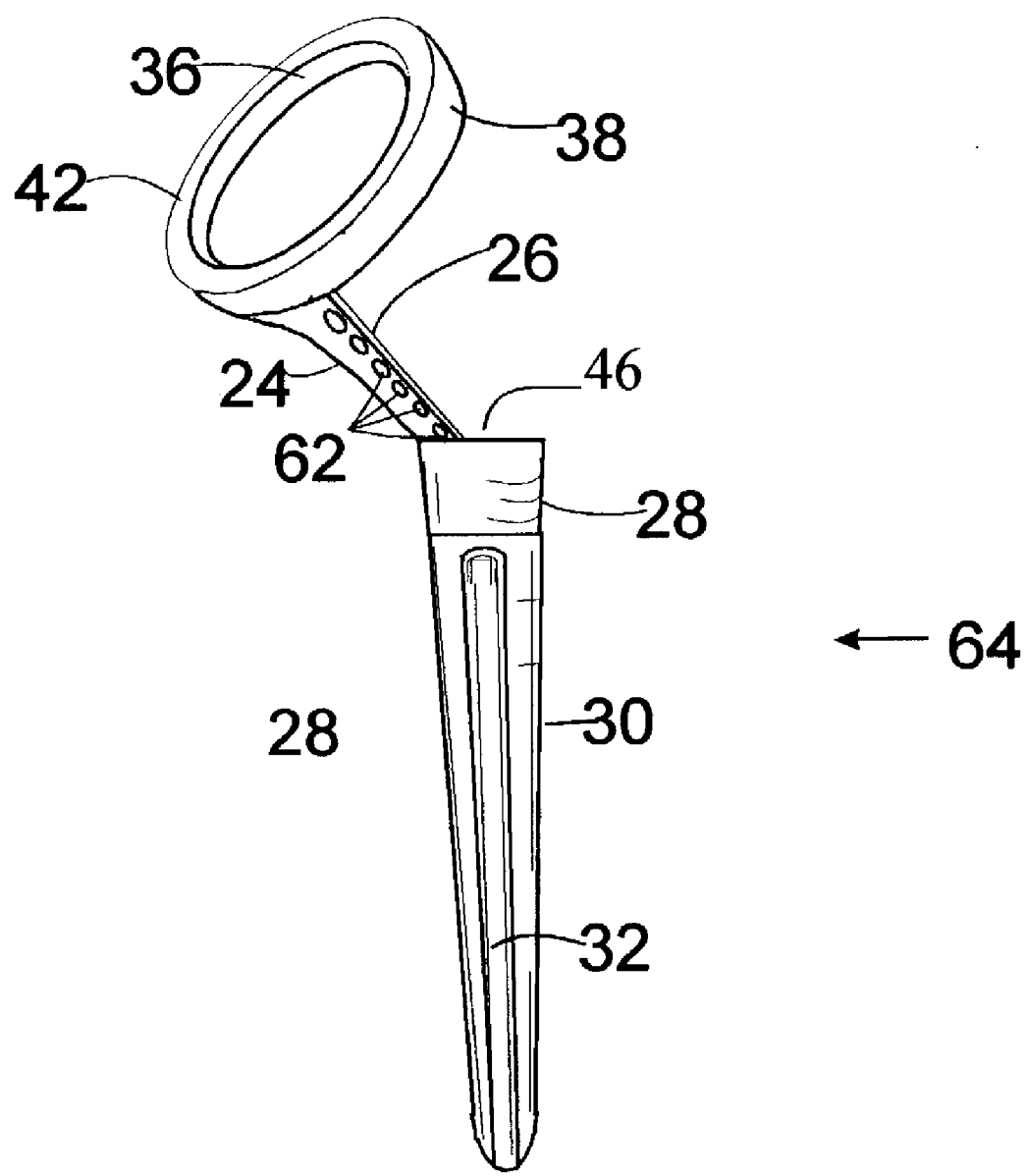
FIG. 5: a perspective view of the prosthesis showing the upper aspect and the inside of the ring.

FIG. 4-B is a cross-section of the medial pillar 24 along a 48—48 line of FIG. 4-A showing that its is an arc of a circle with on its lateral aspect a coating of a material 26 that allows for bone ingrowth;

FIG. 5 is a perspective view of the prosthesis 64 according to the invention. The coating of the ring 38 is visible on its upper 42 and inner 36 aspects. The superior aspect 46 of the stem 22 is slightly hollow with a coating of a material that allows for bone ingrowth.

Figure 6:
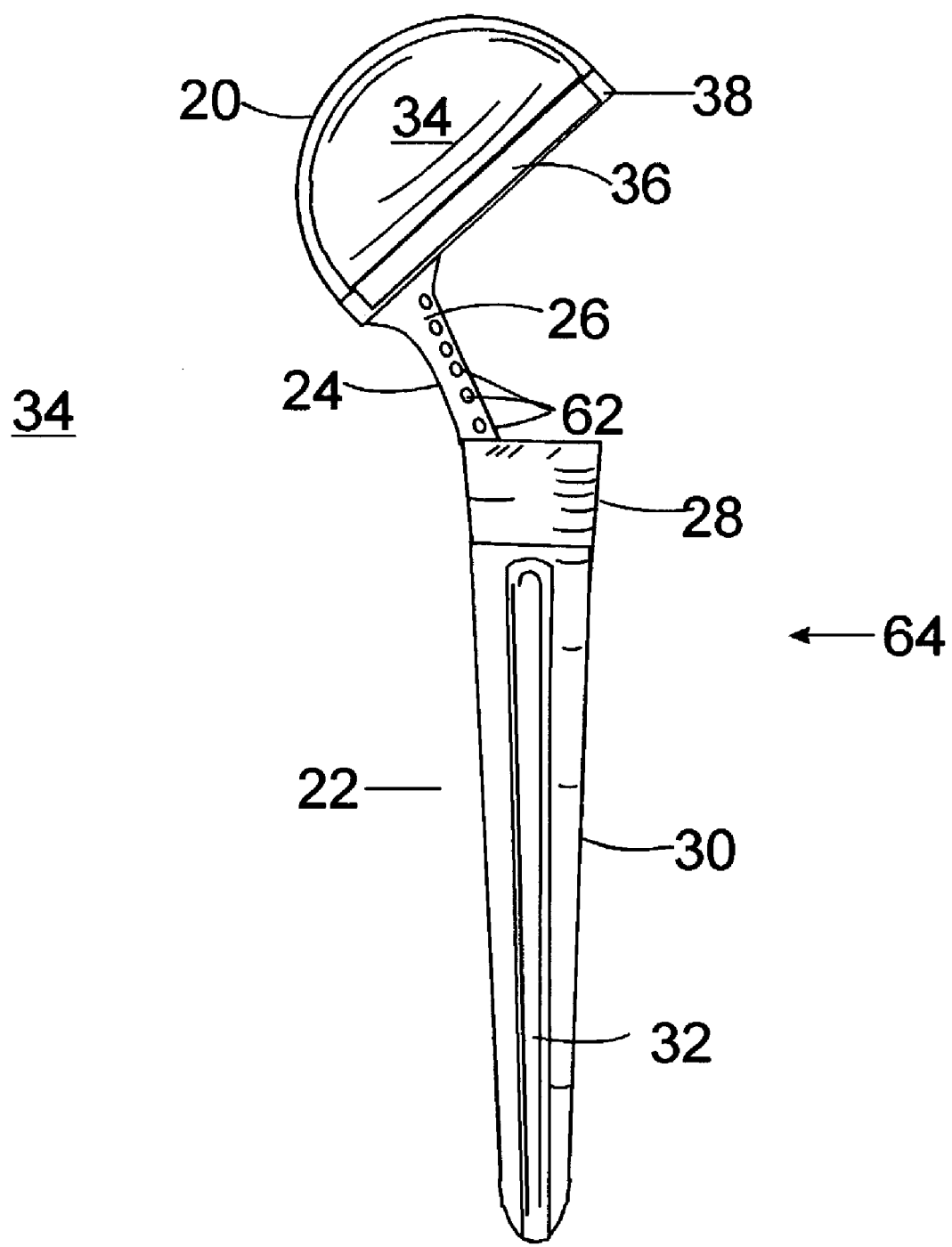
FIG. 6: a sectional view of the head and ring of the prosthesis, showing the inside of the head and of the ring.

FIG. 6 shows a sagittal sectional view of the spherical cap 20 and of the ring 38 along the 40—40 line of FIG. 3 showing the inner lining 34 of the cap and the inner lining 36 of the ring.

Figure 7:
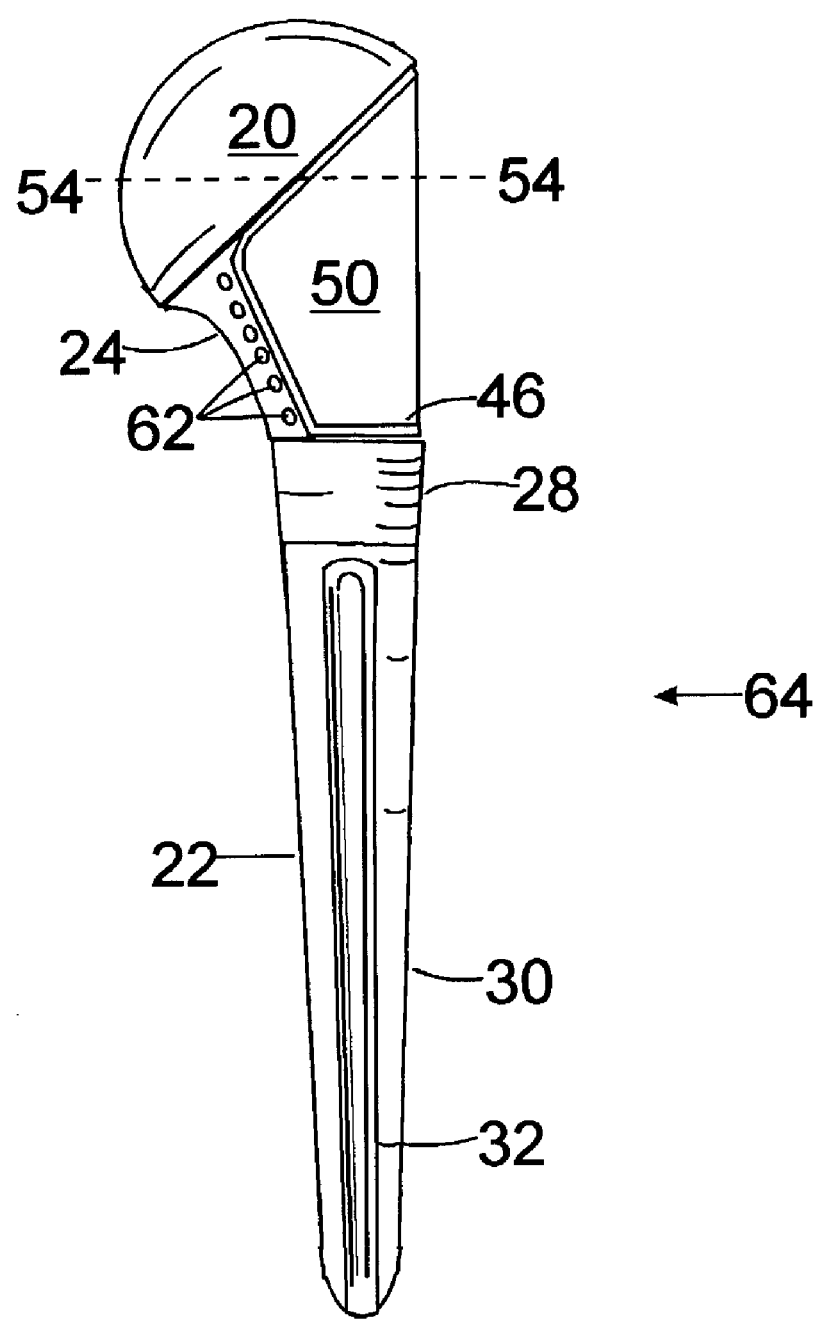
FIG. 7: a front elevational view of the prosthesis fitted with a bone graft.

FIG. 7 shows the prosthesis 64 ready for implantation with a solid bone graft 50 fitted in the epiphyso-metaphyseal space delineated by the hollow cap 20, the lateral aspect of the medial pillar 24 and the superior aspect of the stem 46.

FIG. 8-A shows a sagittal sectional view along the 40—40 line of FIG. 3 of the upper part of the prosthesis 64 showing the epiphyso-metaphyseal space 18 extending from the spherical cap 20 to the upper part of the stem 46.

FIG. 8-B shows a sagittal sectional view along the 40—40 line of FIG. 3 of the upper part of the prosthesis 64, with a solid bone graft 50 being fitted in and the spherical cap 20 filled with bone chips 52 and the continuity of bone from the head 20 to the upper part of the stem 46.

Figure 9:
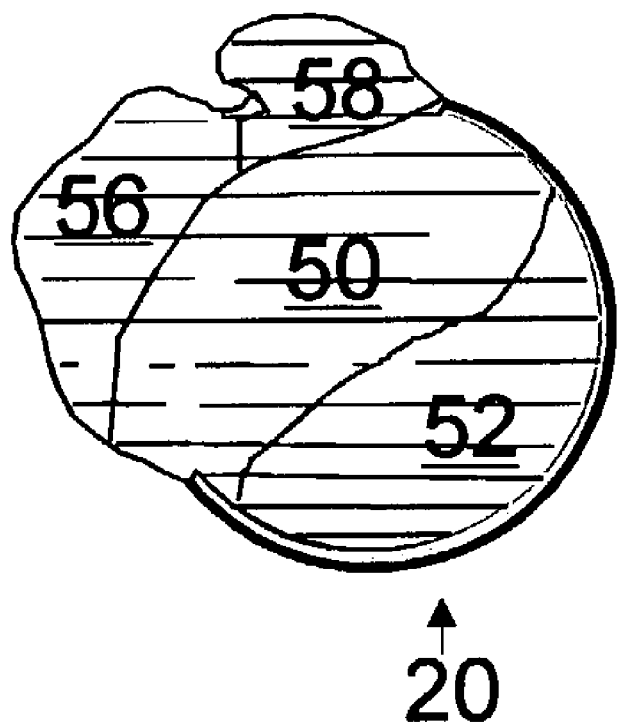
FIG. 9: a sectional view of the proximal part of the prosthesis showing the filling of the head, the bone graft, and the tuberosities in position.

FIG. 9: a transaxial section of the spherical cap 20, along the 54—54 line of FIG. 7, showing the positioning of the greater tuberosity 56 and of the lesser tuberosity 58 with respect to the bone graft 50 and the bone chips 52 filling the head.

Figure 10:
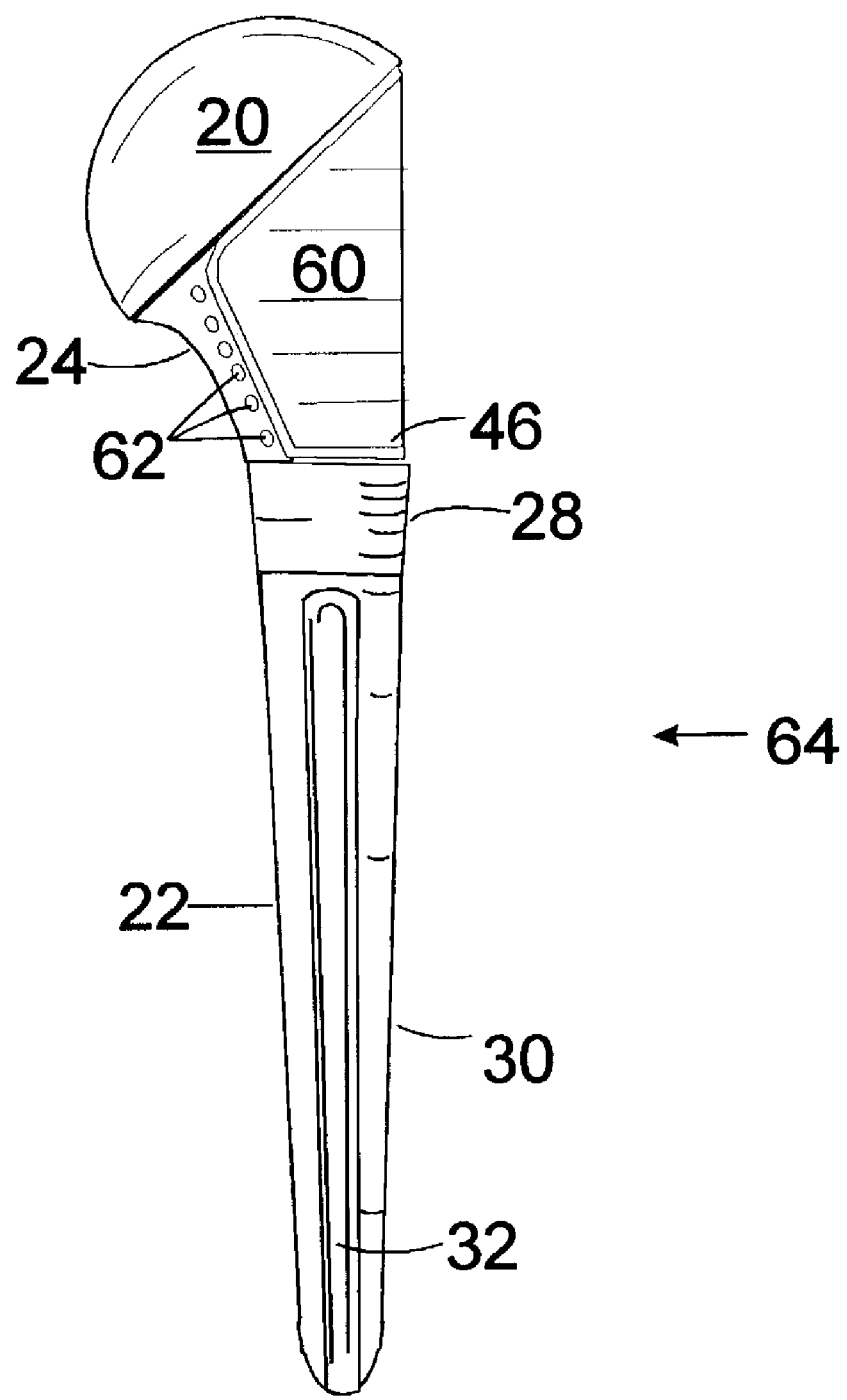
FIG. 10: a front elevational view of the prosthesis fitted with a scaffold of osteoconductive material.

FIG. 10 shows the prosthesis 64 ready for implantation with a scaffold of osteoconductive material 60.

The invention claimed is:
1. A shoulder prosthesis for upper humeral fractures comprising:
a. a stem to be inserted in the medullary canal of the upper humerus;
b. an intermediary section, which is an upward extension of the stem, said intermediary section consisting of a medial curved pillar;

c. a ring fixed at an angle to the upper end of said medial pillar;
d. a generally spherical cap, which is the modular head of the prosthesis, said cap attachable to said ring;
e. an epiphyso-metaphyseal space, said space delineated between an upper aspect of the stem, lateral aspects of the medial pillar, and an inside of the spherical cap, wherein medial, superior, and inferior boundaries of said space are provided with a coating of an osteoconductive material.

2. The shoulder prosthesis of claim 1, said stem comprising two slightly tapered longitudinal groove means to facilitate efficient cementation and having on its most upper pad a coating of osteoconductive material.

3. The shoulder prosthesis of claim 2, said most upper part of the stem being free of cement.

4. The shoulder prosthesis of claim 2, said stem being provided for cement-less fit within the medullary canal of the humerus.

5. The shoulder prosthesis of claim 1, said medial pillar having a concavity, which is its medial aspect, being smooth and polished, and being coated with a lining of an osteoconductive material on its lateral aspect, said medial pillar further having a C-shaped cross-section that ensures more resistance to bending stresses and said medial pillar further having a plurality of holes means of fixation.

6. The shoulder prosthesis of claim 1, said ring attached to the medial pillar having upper, lower and inner surfaces coated with an osteoconductive material and an outer surface without coating.

7. The shoulder prosthesis of claim 1, said spherical cap being hollow,having a polished outer surface, being attachable to the ring and having an inner surface coated with a coating of an osteaconductive material.

8. The shoulder prosthesis of claim 1, said ring attached to the medial pillar having upper, lower and inner surfaces coated with a coating of an osteoconductive material and an outer surface without coating. said spherical cap being hollow, having a polished outer surface, being attachable to the ring and having an inner surface coated with a coating of an osteoconductive material, such that after the spherical cap is attached on the ring, mere is a continuity of the osteoconductive inner coating of said ring and said modular head.

9. The shoulder prosthesis of claim 8 wherein said epiphyso-metaphyseal space, delineated between the upper aspect of the stem, the lateral aspect of the medial pillar and the inside of the spherical cap, and coated with an osteoconduodve material, accommodates a solid autogenous bone graft.

10. A method of treating a fracture of an upper humerus, comprising a separation of a hurneral head and of tuberosities, said method comprising a plurality of steps:
a. harvesting an autogenous iliac bone graft;
b. removing a broken humeral head,
c. providing a shoulder prosthesis as claimed in claim 1, and [d.]filling with said iliac bone graft and chips from said broken humeral bead the space coated wit an osteoconductive material of the shoulder prosthesis,
d. [e.] inserting and cementing said shoulder prosthesis,
e. [f.] attaching separated portions of tuberosities of the broken upper part of the humerus to the remainder of the humerus, to said shoulder prosthesis and between themselves.

11. The method of claim 10, wherein said attaching step uses step uses additional attaching means, comprising sutures and wires through a plurality of holes of the medial pillar to provide optimum stability to the construct.

12. The shoulder prosthesis of claim 1, wherein said epiphyso-metaphyseal space is provided with a scaffold comprising an osteocorlductive material.

13. A method of treating a fracture of an upper humerus comprising a separation of a humeral head and of tuberosities, said method comprising a plurality of steps:
a. removing a broken humeral head,
b. harvesting bone chips from the broken humeral head,
c. providing a shoulder prosthesis as claimed in claim 12,
d. filling with said bone chips from said broken humeral head the spaced coated with an osteoconductive material of the shoulder prosthesis,
e. inserting and cementing said shoulder prosthesis,
f. attaching separated portions of tuberosities of the broken upper part of the humerus to the remainder of the humerus, to said shoulder prosthesis and between themselves.

* * * * *